United States Patent
Weissman et al.

(10) Patent No.: US 6,559,299 B2
(45) Date of Patent: May 6, 2003

(54) PREPARATION AND ISOLATION OF INDOLOCARBAZOLE GLYCOSIDES

(75) Inventors: Steven Weissman, Short Hills, NJ (US); David Tschaen, Holmdel, NJ (US); Asayuki Kamatani, Okazaki (JP); Shouichi Hiraga, Okazaki (JP); Masashi Kawasaki, Okazaki (JP); Takehiko Iida, Okazaki (JP)

(73) Assignees: Merck & Co., Inc., Rahway, NJ (US); Banyu Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 10/103,081

(22) Filed: Mar. 21, 2002

(65) Prior Publication Data

US 2002/0193324 A1 Dec. 19, 2002

Related U.S. Application Data

(60) Provisional application No. 60/279,629, filed on Mar. 29, 2001.

(51) Int. Cl.⁷ .................. C07H 19/00; C07H 19/22; C07H 15/00; C07H 5/04; C07H 19/16
(52) U.S. Cl. .................. 536/27.1; 536/17.7; 536/18.7; 536/22.1; 536/27.11; 536/27.12; 536/29.1
(58) Field of Search .................. 536/17.7, 18.7, 536/22.1, 27.1, 27.11, 27.12, 29.1

(56) References Cited

U.S. PATENT DOCUMENTS

| 5,437,996 A |   | 8/1995 | Kojiri et al. |
|---|---|---|---|
| 5,589,365 A |   | 12/1996 | Kojiri et al. |
| 5,591,842 A |   | 1/1997 | Kojiri et al. |
| 5,599,808 A | * | 2/1997 | Goldstein et al. |
| 5,621,098 A | * | 4/1997 | Heath et al. |
| 5,668,271 A |   | 9/1997 | Kojiri et al. |
| 5,804,564 A |   | 9/1998 | Kojiri et al. |
| 5,922,860 A |   | 7/1999 | Kojiri et al. |

FOREIGN PATENT DOCUMENTS

EP 0 545 195 B1 11/1995

OTHER PUBLICATIONS

Zembower, D.E., et al., Bioorg. Med. Chem. Lett. 1999, 9, 145.
Ohkubo, M., et al., Biorg. Med Chem. Lett. 1999, 9, 3307.
Nishimura, S., et al., Tetrahedron 1996, 52, 8099.
Seela, G., et al., J. Org. Chem. 1982, 47,226.
Seela, F., et al., J. Chem. Soc., Perkin Trans. 1 1988, 697.
Seela, F., et al., J. Org. Chem., 1987, 52, 5136–5143.
Seela, F., et al., Synthesis 1990, 945–950.
Barco, A., Synthesis 1976, 124.
Bocchi, V., et al., Synthesis 1976, 414.
Long, et al., Exp. Opin. Ther. Pat. (2000) 10(5), pp. 635–666.
Ohkubo, et al., Bioorg. Med. Chem. Lett. (2000), 10, pp. 419–422.
Prudhomm, Curr. Med. Chem. (2000), 7, pp. 1189–1212.
Ghali, et al., J. Org. Chem. (1981), 46, pp.5413–5414.
Csuk, et al., Tetrahedron (1999), 55, pp. 739–750.
Gilbert, et al., J. Org. Chem. (1999), 64, pp. 5670–5676.
Stott, et al., J. Am. Chem. Soc. (1995), 117, pp. 4199–4200.
Granata, et al., Carbohydrate Research (1980), 86, pp. 305–308.
Ohkubo, et al., Tetrahedron (1997), vol. 53, No. 2, pp. 585–592.
Akao, et al., Tetrahedron (2001), vol. 57, pp. 8917–8923.

* cited by examiner

*Primary Examiner*—James O. Wilson
*Assistant Examiner*—Traviss C. McIntosh
(74) *Attorney, Agent, or Firm*—Dianne Brown; Mark R. Daniel

(57) ABSTRACT

The present invention relates to a novel process to make indolocarbazole glycosides in high purity which inhibit the growth of tumor cells and are therefore useful in the treatment of cancer in mammals, and the like.

12 Claims, No Drawings

PREPARATION AND ISOLATION OF INDOLOCARBAZOLE GLYCOSIDES

This application claims the benefit of Provisional application Ser. No. 60/279,629 filed Mar. 29, 2001.

BACKGROUND OF THE INVENTION

The present invention relates to a novel process to make indolo-carbazole carbazole glycosides in high purity which inhibit the growth of tumor cells and are therefore useful in the treatment of cancer in mammals, and the like.

In the field of cancer chemotherapy, a large number of compounds have already been put to practical use as antitumor agents. However, a need continues for the development of more efficacious compounds that work against a variety of tumors (see the Proceedings of the 47th General Meeting of the Japan Cancer Society, pp. 12–15 (1988)). This need has led to the development of indolocarbazole derivatives. (See U.S. Pat. Nos. 4,487,925; 4,552,842; 4,785,085; 5,591,842 and 5,922,860; Japanese Patent No. 20277/91; Journal of Antibiotics, Vol. 44, pp. 723–728 (1991); W091/18003; WO 98/07433; and EP0545195 A1). These compounds have been shown to act as topoisomerase inhibitors and therefore useful in the treatment of cancer (Cancer Chemother. Pharmacol. 34 (suppl): S41-S45 (1994)).

The success of these compounds in treating numerous cancers has necessitated the development of improved methods for their syntheses. (see Bioorg. & Med. Chem. Letters 2000, 10, 419; Tetrahedron 1997, 53, 5937; Tetrahedron 1997, 53, 585; and Synthesis 1976, 414). The previously known methods, however, suffer from numerous problems, including the use of undesirable solvents, mercury or silver salts, low yields and formation of unwanted side-products necessitating tedious or protracted purification steps.

For example, the previously known methods of preparation of the indolocarbazole glycoside III in high purity require purification procedures, such as combinations of carbon treatment, chromatography and/or recrystallization of the crude material, that are tedious, time-consuming and dangerous, especially when performed on a commercial scale due to the highly cytotoxic nature of the product. (see Bioorg & Med Chem Letters 1999, 3307; and Tetrahedron 1997, 585 (describing synthesis of structurally similar compound, requiring re-dissolution of crude product to obtain pure material)).

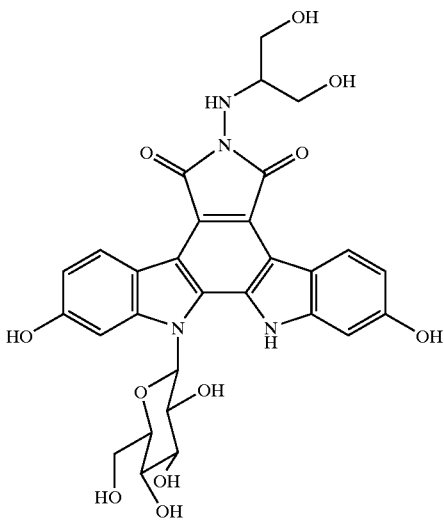

An object of this invention therefore is to provide a novel route to these indolopyrrolocarbazole-derived antitumor substances while overcoming the problems inherent in the previously known syntheses, specifically a route producing the product in sufficient purity to allow for use "as is" in subsequent formulations.

SUMMARY OF THE INVENTION

The present invention relates to a novel process to make indolo-carbazole glycosides of Formula I in high purity which inhibit the growth of tumor cells and are therefore useful in the treatment of cancer in mammals, and the like.

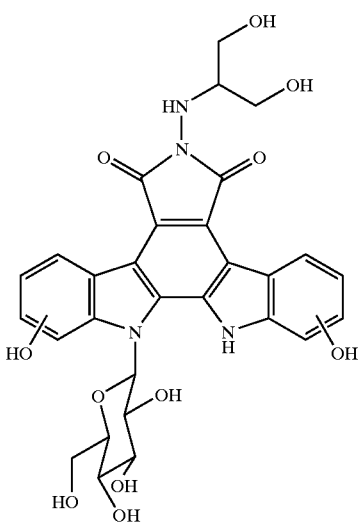

DETAILED DESCRIPTION OF THE INVENTION

An embodiment of the present invention is illustrated by a process for the preparation of a compound of Formula I in high purity,

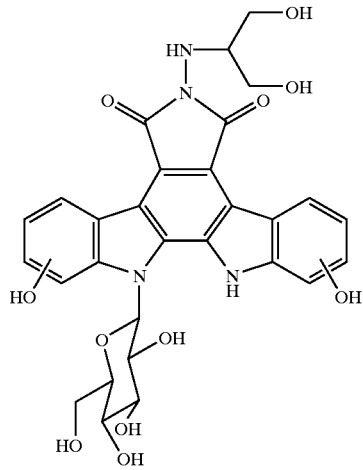

I which comprises the steps of:

(a) adjusting the pH of an acidic mixture consisting essentially of an alcohol, an acid, water and compound I, by adding a base to produce a solution with a pH in the range of about 1.5 to about 6.5;

(b) keeping the temperature of the solution from step (a) in the range of about 50° C. to about 100° C. ; and (c) isolating the crystals of compound I.

In a second embodiment of the instant invention, the process comprises the steps of:

(a) adjusting the pH of an acidic mixture consisting essentially of an acid, alcohol, water and compound I, by adding a base to produce a solution with a pH in the range of about 1.5 to about 6.5;

(b) adjusting the solution from step (a) with an alcohol so that the solution is about 10% w/v to about 30% w/v water in an alcohol and the concentration of compound I is about 10 mL/g to 20 mL/g;

(c) adjusting the temperature of the solution from step (b) to a temperature in the range of about 50° C. to about 100° C. ;

(d) adding an alcohol to the solution from (c) such that the solution is diluted to about 3:2 (solution: alcohol);

(e) aging the solution from (d) at a temperature in the range of about 50° C. to about 100° C. until crystals of compound I are formed to produce a slurry; and (f) isolating the crystals of compound I.

In a further embodiment of the second embodiment, the process further comprises deprotecting intermediate II:

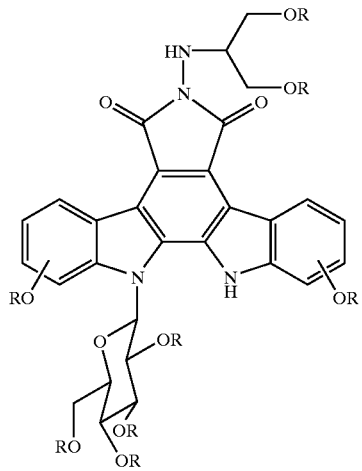

II (wherein R is independently a hydrogen or a substituted or unsubstituted benzyl protecting group, with the proviso that at least one R is a substituted or unsubstituted benzyl protecting group), via hydrogenation in the presence of a catalyst to produce a reaction mixture, followed by filtering the reaction mixture to afford the mixture of step (a).

In an alternative embodiment, R is benzyl in the process described above.

In a third embodiment of the instant invention, the process for the preparation of compound m in high purity

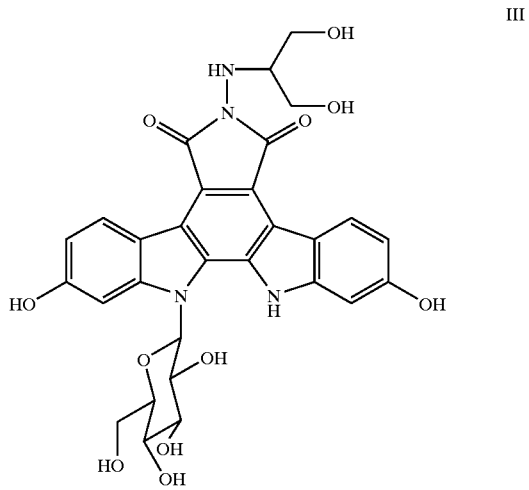

III comprises the steps of:
(a) adjusting the pH of an acidic mixture consisting essentially of an acid, alcohol, water and compound III, by adding a base to produce a solution with a pH in the range of about 1.5 to about 6.5;
(b) adjusting the solution from step (a) with an alcohol so that the solution is about 10% w/v to about 30% w/v water in an alcohol and the concentration of compound III is about 10 mL/g to 20 mL/g;
(c) adjusting the temperature of the solution from step (b) to a temperature in the range of about 50° C. to about 100° C. ;
(d) seeding the solution;
(e) adding an alcohol to the solution such that the solution is diluted to about 3:2 (solution: alcohol);
(f) aging the solution from (e) at a temperature in the range of about 50° C. to about 100° C. until crystals of compound III are formed to produce a slurry; and
(g) isolating the crystals of compound III.

In a further embodiment of the third embodiment, the process further comprises deprotecting intermediate II:

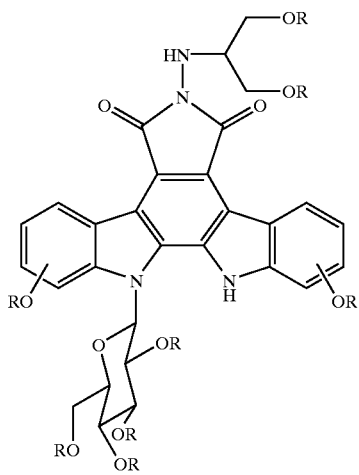

(wherein R is independently a hydrogen or a substituted or unsubstituted benzyl protecting group, with the proviso that at least one R is a substituted or unsubstituted benzyl protecting group), via hydrogenation in the presence of a catalyst to produce a reaction mixture, followed by filtering the reaction mixture to afford the mixture of step (a).

And yet another embodiment is the process described immediately above wherein the pH in step (a) is adjusted to a pH in the range of about 1.5 to about 3.5; the solution in (b) is adjusted so that the solution is about 15% w/v to about 25% w/v water in alcohol and the concentration of compound III is about 12 mL/g to about 18 mL/g; and the temperature in step (c) is adjusted to about 70° C.

A further embodiment is the process above wherein the pH in step (a) is adjusted to a pH of about 2.5; the solution in (b) is adjusted so that the solution is about 20% w/v water in alcohol and the concentration of compound III is about 15 mL/g; and the temperature in step (c) is adjusted to about 70° C.

Also encompassed by the present invention is the process described above further comprising the step of adjusting the slurry after step (f) such that the water content is lowered to a range of about 1% w/v to about 10% w/v before isolating the crystals of compound III in step (g).

A preferred embodiment is a process for the preparation of compound III in high purity,

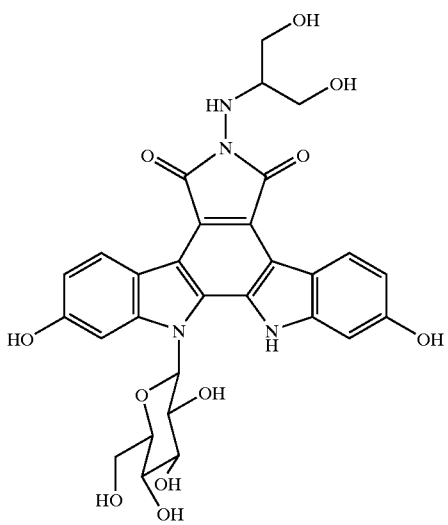

which comprises the steps of:
(a) adjusting the pH of an acidic mixture consisting essentially of an acid, alcohol, water and compound III, by adding a lower alkyl amine base to produce a solution with a pH of about 2.5;
(b) adjusting the solution from step (a) with isopropyl alcohol so that the solution is about 20% w/v water in isopropyl alcohol and the concentration of compound I is about 15 mL/g;
(c) adjusting the temperature of the solution from step (b) to a temperature of about 70° C.;
(d) seeding the solution;
(e) adding isopropyl alcohol to the solution such that the solution is diluted to about 3:2 (solution:isopropyl alcohol);
(f) aging the solution from (e) at a temperature of about 70° C. until the crystals of compound I are formed to produce a slurry;
(g) adjusting the slurry so that the water content is about 3% w/v;
(h) aging the slurry at about 70° C. before cooling down to about 22° C.; and
(i) isolating the crystals of compound III.

In a further embodiment of the preferred embodiment, the process further comprises deprotecting intermediate II:

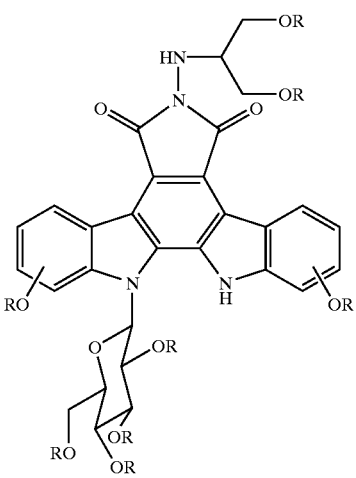

(wherein R is independently a hydrogen or a substituted or unsubstituted benzyl protecting group, with the proviso that at least one R is a substituted or unsubstituted benzyl protecting group), via hydrogenation in the presence of a catalyst to produce a reaction mixture, followed by filtering the reaction mixture to afford the mixture of step (a).

Also within the scope of the present invention is the process described immediately above wherein the lower alkyl amine in step (c) is triethylamine.

The present invention generates product which can be directly crystallized from the reaction medium without additional purification steps. In addition, the presently claimed process affords crystals with a more stable crystal geometry, 3-D trapezoid, than the previously known methods, 2-D needles, as suggested by solubility kinetics.

Compound I and Compound III may be synthesized following the procedure described in U.S. Pat. No. 5,591,842, issued Jan. 7, 1997, herein incorporated by reference. The powder of Compound III, which is obtained by the process described in WO 95130682 and U.S. Pat. No. 5,591,842, is crystallized by the method of the instant invention.

As used in the present application, "high purity" refers to product which is obtained with 1% or less total impurities as measured by HPLC.

An "acidic mixture" refers to a mixture that has a pH that is less than about 7.0. Most preferably, the pH of the acidic mixture is less than about 2.5.

For the present application, types of acids that can be used include, but are not limited to, anhydrous or aqueous HF, HCl, HBr, HI, $HNO_3$, $HClO_4$, sulfuric, phosphoric, propionic, MsOH, TsOH, mono-phosphate salt, di-phosphate salt, mixed phosphate salt, carboxylic acids or ammonium halides. A mixed phosphate salt can be illustrated as $M_1M_2HPO_4$, where $M_1$ and $M_2$ are independently selected from H, Na, K, $NH_4OH$, sodium potassium, and the like. More preferably, the acids are selected from HCl.

The choice of catalyst in the hydrogenolysis reactions described herein will be readily apparent to the skilled artisan. Suitable catalysts include palladium on carbon, $Pd(OH)_2$, Raney Nickel, tungsten catalysts, $Rh/Al_2O_3$, and the like. Palladium catalysts are preferred, such as palladium on carbon.

"Seeding" refers to the exposure of a solution to crystals (seed crystals) in order to catalyze the precipitation of crystals from the solution. Seeding can be done by addition of the seed crystals in a solid, dry form or the seed crystals may be added in the form of a slurry in a liquid. "Seed crystals" may be crystals of the same compound being induced to precipitate or they may be of a different compound. In the present case, seeding with a slurry of the same compound is preferred.

"Aging" means to maintain the solution being aged at a constant temperature and volume for a certain period of time. The amount of time the reactions are aged in the present invention is not critical, unless specifically noted otherwise, and can be readily discerned by those skilled in the art.

"Filtering" means to pass the solution through some medium so that particulate matter is removed. The choice of medium is not critical and can be readily chosen by the average practitioner. Filtering may be accomplished by passing through celite, solka floc, sand, glass frit, diatomaceous earth, and the like.

"Alcohol" is intended to mean an organic molecule of 1 to 5 carbons, in a straight or branched chain, with at least on hydroxyl group as the prominent active group. Alcohol includes methanol, propanol, isopropanol, butanol, sec-butanol, etc. Isopropyl alcohol is the preferred alcohol.

The term "substituted benzyl protecting group" includes, but is not limited to, p-MeO-benzyl, o-nitrobenzyl, p-nitrobenzyl, p-halobenzyl (wherein halo includes, chloro, bromo, and iodo), 2,6-dichlorobenzyl, diphenylmethyl, triphenylmethyl, and the like. Further suitable protecting groups may be found in *Protective Groups in Organic Chemistry* by Peter G. Wuts and Theodora W. Greene, John Wiley & Sons, $3^{rd}$ed. (1999).

The present invention comprises a step where the pH of a filtrate is adjusted to a particular range. The pH may be adjusted with any suitable base, such as triethylamine, diIsopropylethylamine, tributylamine, pyridine, 2,6-lutidine, 2,4,6-collidine, DBU, DBN, diisopropylamine, N,N-dimethylaniline, DABCO, N-alkylmorpholine, and the like. Lower alkyl amine bases are preferred. Triethylamine is the most preferred.

"Slurry" refers to a suspension of solid or crystals in a liquid. The solid may be partially, incompletely, or completely non-dissolved in the liquid.

Synopsis of Schemes

Scheme A illustrates a generalized approach to the preparation of biologically active indolocarbazole glycosides via a deprotection/crystallization protocol to afford product in high yield and high purity, obviating the need for further purification steps before formulation.

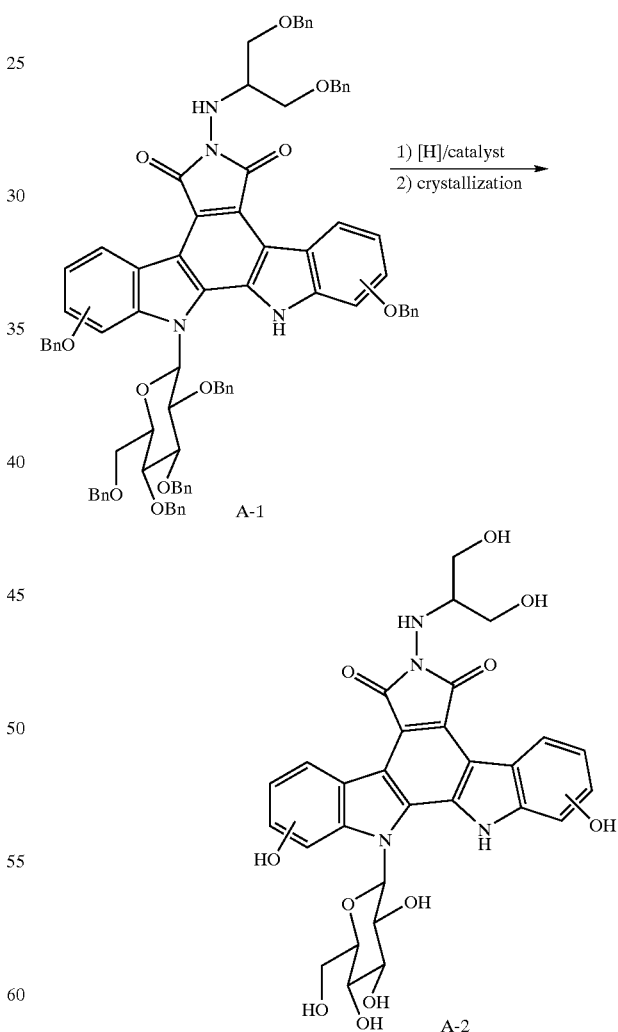

SCHEME A

EXAMPLES

Examples provided are intended to assist in a further understanding of the invention. Particular materials employed, species and conditions are intended to be further illustrative of the invention and not limiting of the reasonable scope thereof.

Example 1

The method for the production of Compound 1-1 is described in WO95/30682 (Equivalent: U.S. Pat. No. 5,804,564), hereby incorporated by reference.

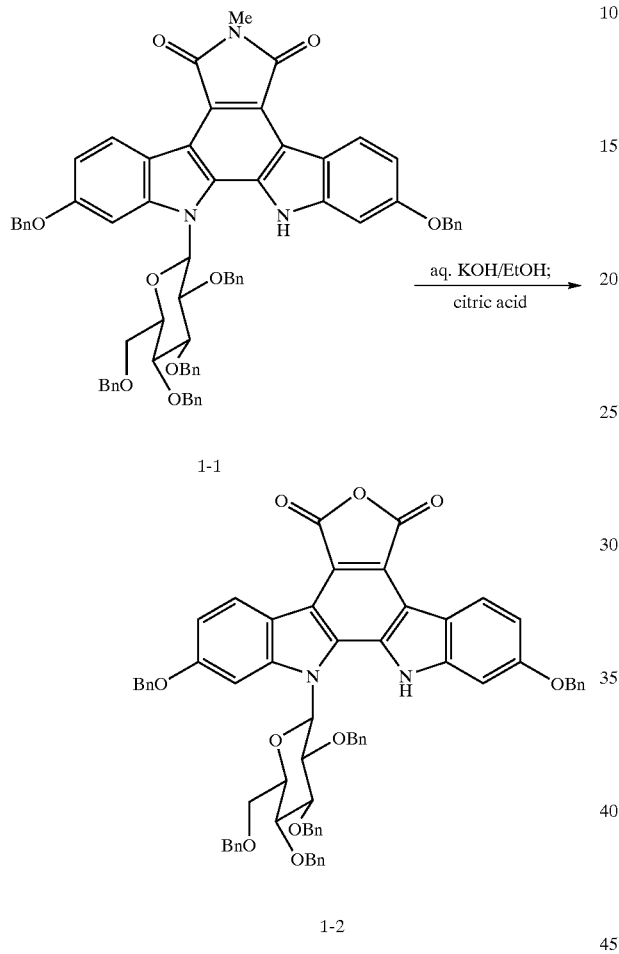

Ethanol (14.0 L) was added dropwise to a biphasic mixture of compound 1-1 (1.55 kg, 1.44 mol), toluene (5.6 L) and 48% aqueous KOH (4.15 kg) in a 50-L glass vessel over 0.5 hour at room temperature, keeping the internal temperature below 30° C. The resulting dark red mixture was stirred at 20–30° C. for 12 hours, during which time the mixture became homogeneous red solution. The mixture was then further aged at −5° C. for 1 hour, upon which time 10% aqueous citric acid (23.5 kg) was added slowly to form a pH 7.7–8.0 mixture, keeping the internal temperature below 5° C. The resulting mixture was warmed and stirred at 25–30° C. for 7 hours, during which time an additional 10% aqueous citric acid (1.77 kg) was added periodically to maintain pH at 7.5–8.0. The mixture was then extracted with MTBE (15.5 L), and the separated organic layer was washed with 3% aqueous NaCl (2×3.1 L) and 25% aqueous NaCl (3.1 L), dried ($Na_2SO_4$) and treated with carbon (Darco G-60, 155 g, room temperature, 1 hour). The filtered solution was concentrated in vacuo to the 6-L level, and MeCN flushes (2×15 L) was performed, each time concentrating in vacuo to a 6-L batch volume (residual toluene: 9%). The mixture was then diluted with MeCN to make a 23.3 L solution, and MeOH (3.0 L) was added slowly over 0.5 hour at 22–25° C. followed by a seed of product (1–2), which initiated crystallization. The resulting mixture was further aged at this temperature range for 1 hour, followed by a slow addition of MeOH (17.6 L) over 1 hour. The resulting yellow suspension was aged at 22–25° C. for 1 hour followed by further aging at 0–5° C. for 3 hours. The crystals were isolated by filtration, washed with a 9:1 (v/v) mixture of MeCN/MeOH (15.5 L) and dried in vacuo to afford 1–2.

$^1$H—NMR (270 MHz, $CDCl_3$, ppm): 10.79 (1H, br. s,), 9.04 (1H, d, J=9.2 Hz), 8.95 (1H, d, J=9.6 Hz), 7.26 (32H, m), 6.17 (2H, d, J=7.3 Hz), 5.85 (1H, d, J=8.2 Hz), 4.89 (10H, m), 4.32 (1H, t, J=8.9 Hz), 3.96 (6H, m), 3.13 (1H, d, J=10.2 Hz)

Example 2

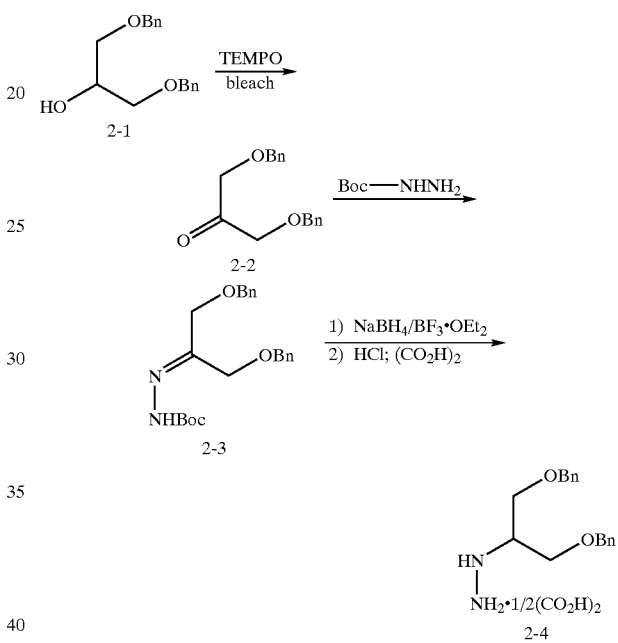

12.1% aqoueous NaClO (titrated using aqueous $Na_2S_2O_3$ prior to use; 4.06 kg, 6.61 mol) was added dropwise to a stirred mixture of 1,3-dibenzyloxy-2-propanol (compound 2-1, 1.50 kg, 5.51 mol), 2,2,6,6-tetramethyl-1-piperidinyloxy free radical (TEMPO, 86.0 g, 0.550 mol), MeCN (20.6 L) and 3% aqueous $NaHCO_3$ (15.5 kg, 5.51 mol) in a 50-L glass vessel at 0° C. over 1.5 hours, keeping the internal temperature at 0–5° C. The resulting mixture was stirred for an additional 1 hour at 0–5° C. and extracted with MTBE, methy t-butyl ether, (41 L) below 10° C. The separated organic layer was washed with 10% aqueous $Na_2SO_3$ (5.0 kg) below 10° C. followed by 5% aqueous NaCl (3.0 kg) and 1% aqueous NaCl (3.0 kg) at room temperature. The pale red organic layer was then assayed by HPLC and calculated to contain 1.48 kg (5.49 mol) of the desired ketone (compound 2-2). The solution was then placed in the 50-L vessel and concentrated in vacuo (40° C. bath) to ca. 8 L with flushes of n-heptane (2×7.5 L) to make a heptane mixture (residual MTBE and MeCN are 0.005% and 0.90% respectively) followed by diluting with n-heptane to form a 37.5-L batch volume. The mixture was then warmed to 70° C. , and a solution of Boc-$NHNH_2$ (801 g, 6.06 mol) and toluene (1.5 L) was added. The resulting mixture was stirred above 70° C. for 3 hours, followed by cooling to 60° C. A seed of product (compound 2-3) was added, and the resulting mixture was aged at 59–61° C. for 1 hour to initiate crystallization. The mixture was then allowed to cool to room temperature and aged overnight. The crystals were isolated by filtration at 20° C., washed with n-heptane (7.5 L) followed by a 7:3 v/v mixture of n-heptane/i-PrOH (4.5 L) and n-heptane (4.5 L), and dried in vacuo to provide compound 2-3 as colorless needles.

A solution of compound 2-3 (1.64 kg, 4.27 mol) and THF (5.9 L) was then added dropwise to a stirred suspension of NaBH$_4$ (364 g, 9.62 mol) and THF (7.2 L) in a 50-L glass vessel at 0° C., keeping the internal temperature below 5° C. BF$_3$.OEt$_2$ (920 g, 6.48 mol) was then added dropwise to the resulting mixture, keeping the internal temperature below 10° C. The resulting colorless suspension was stirred at 0–5° C. for 1 hour, upon which time 6 N aqueous HCl (4.29 kg, 23.5 mol) was added dropwise over 1 hour, keeping the internal temperature below 20° C. (Caution: vigorous gas evolution). The resulting colorless suspension was warmed and stirred at 60–65° C. for 2 hours, until which time the gas evolution ceased. Degassed 2 N aqueous NaOH (12.9 L, 25.8 mol) was then added slowly to the mixture at 3° C., keeping the internal temperature below 20° C., followed by warming the resulting mixture to room temperature and extraction using degassed MTBE (40 L). The separated organic layer was washed with degassed water (6.6 L) followed by degassed brine (6.5 L) and degassed water (3.3 L). The organic layer was then diluted with degassed MTBE to form a 57-L solution, and a seed of product (compound 2-4) was added followed by a solution of oxalic acid (177 g, 1.97 mol) and degassed MTBE (1.97 L) dropwise over 15 minutes, which crystallized the product. The resulting colorless slurry was aged at room temperature overnight, and the crystals were isolated by filtration, washed with MTBE (12.3 L) and dried in vacuo to provide compound 2-4 (1.25 kg, 88%, 99.9 area % by HPLC) as colorless plates.

$^1$H—NMR (270 MHz, DMSO-d$_6$, ppm): 7.41–7.26(m,10H), 5.91–5.62 (br. m, 4H), 4.50 (s, 4H), 3.56 (br. d, J=4.9 Hz, 4H), 3.34 (m, 1H). $^{13}$C—NMR (68 MHz, DMSO-d$_6$, ppm): 164.7, 138.2, 128.2, 127.5, 127.4, 72.3, 68.3, 59.8

Example 3

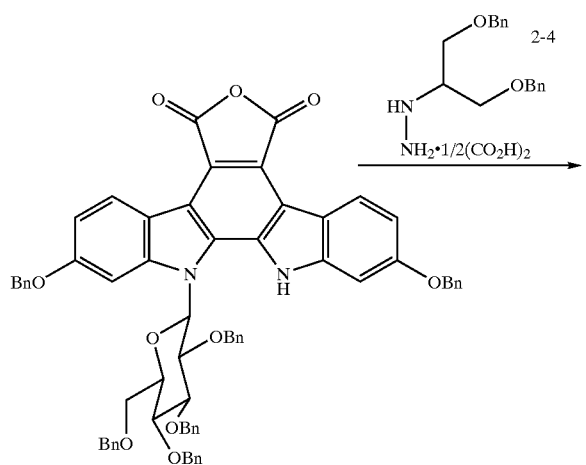

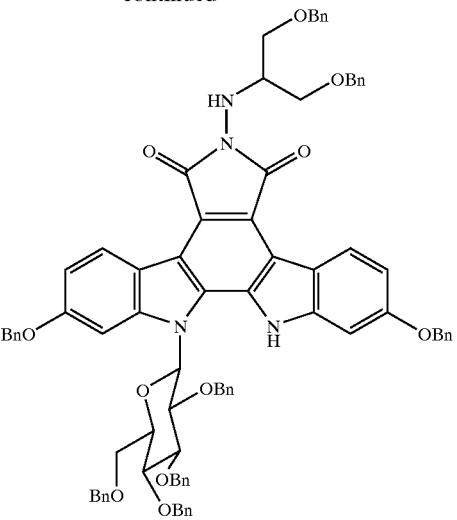

3-1

A 22-liter nitrogen-purged vessel was charged with DMA (8.3 L), compound 1-2 (1.00 kg; 0.94 moles) and compound 2-4 (350 g; 1.06 moles) at 22° C. The resulting slurry was degassed with stirring by applying vacuum to the vessel (40–80 torr) for 5 minutes/cycle and filling with nitrogen (three cycles). The contents were heated to 65° C. over 30 minutes during which time the solution became homogeneous. Triethylamine (146 ml; 1.05 moles) was added rapidly and the solution aged at 65° C. for 3 hours. The contents were cooled to 45° C. and transferred to a 50-L cylindrical vessel containing nitrogen-sparged MTBE (17.0 L) held at 10° C. The contents of the vessel were again cooled to 10° C. and nitrogen-sparged water (4.7 L) was added over 10 minutes to keep the internal temp below 30° C. 2M Hydrochloric acid (440 ml) was added to the biphasic mixture at 22° C. After agitation at 22° C. for 10 minutes, the layers were separated and the organic layer washed with water (3×3.8 L). The organic layer was concentrated in vacuo to the 5 L level (20–25° C.) and multiple THF flushes were performed to remove the MTBE. Removal of the solvent in vacuo produced the desired compound, 3-1.

$^1$H—NMR (270 MHz, CDCl$_3$, ppm): 10.63 (1H, br. s.), 9.24 (1H, br. d, J=9.6 Hz), 9.16 (1H, br. d, J=9.6 Hz), 7.50–6.84 (42H, m), 6.20 (2H, br. d, J=7.6 Hz), 5.84 (1H, d J=8.6 Hz), 5.33 (1H, br. d, J=3.0 Hz), 5.21 (1H, d, J=12.2 Hz), 5.19 (1H, d, J=11.9 Hz), 5.16 (1H, d, J=12.2 Hz), 5.08 (1H, d, J=11.9 Hz), 5.08 (1H, d, J=10.9 Hz), 4.96 (1H, d, J=10.9 Hz), 4.89(1H,d,J=10.9 Hz),4.85(1H, d, J=10.9 Hz), 4.72 (1H, d, J=12.9 Hz), 4.68 (1H, d, J=12.9 Hz), 4.62–4.48 (4H, m), 4.33 (1H, dd, J=9.6, 9.6 Hz), 4.06–3.77 (7H, m), 3.72 (4H, d, J=5.6 Hz), 3.04 (1H, d, J=9.9 Hz).

$^{13}$C—NMR(68 MHz, CDCl$_3$, ppm): 168.8, 168.7, 159.4, 159.3, 143.2, 142.9, 138.0, 137.9, 137.6, 136.9, 136.8, 136.6, 136.0, 130.2, 128.7, 128.6, 128.5, 128.4, 128.3, 128.2, 128.2, 128.1, 128.0, 127.9, 127.8, 127.7, 127.6, 127.5, 127.4, 127.3, 126.9, 126.6, 119.4, 119.1, 118.0, 116.9, 116.7, 116.1, 110.4, 96.7, 96.3, 85.8, 84.7, 80.9, 77.4, 77.2, 76.0, 75.9, 75.4, 74.9, 73.9, 73.3, 73.2, 70.7, 70.4, 69.9, 69.8, 66.7, 58.7, 49,4, 30.9, 27.0

Example 4

Caution: The Product of This Reaction, Compound 4-1, is a Cytotoxic Compound

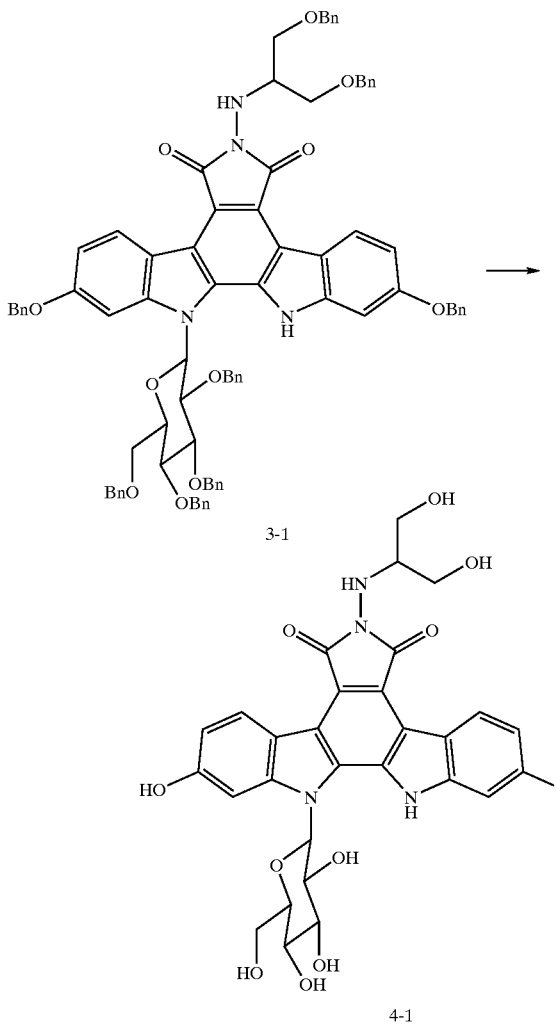

10% Pd on carbon (50% wet; 112 g) was charged to a 5 gallon autoclave, followed by a THF (tetrahydrofuran) solution of 12-β,-D-(2,3,4,6-tetra-O-benzylglucopyranosyl)-12,13-dihydro-2, 10-dibenzyloxy-6-[[-(2-benzyloxy-1 -(benzyloxymethyl) ethyl]amino]-5H-indolo[2,3-a] pyrrolo [3,4-c]carbazole-5,7(6H)-dione (3-1) (175 g/L solution; 6.4 L; 1.12 assay kg), isopropyl alcohol, IPA, (7.9 L) and 3 N HCl (224 mL). The contents were hydrogenated at 40° C./40 psi with rapid agitation for 4–14 hours during which time 110% of the theoretical amount of hydrogen was absorbed. The contents were cooled to 25° C. and the reaction mixture filtered over a bed of solka floc which was rinsed with 3/2 IPA/THF (1×3 L). The filtrate was pH adjusted to 2.5 (range: 1.5–6.5) using 1 M triethylamine in IPA (ca. 600 mL), followed by the addition of water (4.0 L). The batch was concentrated at atmospheric pressure to the 7.5 L level. The distillation was continued at a constant batch volume while feeding in 4/1 IPA/water (6.5 L). The water content was lowered to 20% (w/v) (range 10–30% water) by feeding IPA (ca. 9 L) to the vessel while keeping the batch volume at 7.5 L. The contents were cooled to 70° C. and seed (5.0 g) was added as an IPA slurry (50 mL). The batch was held at 70° C. for 1 hour followed by the addition of IPA (5.0 L) over 90 minutes. The batch was aged at 70° C. for 9–24 hours during which time the bulk of the product crystallized. A constant volume distillation feeding in IPA (17 L) was performed that resulted in lowering the water content to 3% (w/v) (range 1–10% water). The slurry was aged at 70° C. for 3–6 hours followed by cooling to 22° C. and aging for 1 hour. The slurry was filtered and the cake washed with IPA (2.5 L) and then methanol (1.5 L), followed by in vacuo drying at 38° C. for 6 hours to provide the product, 4-1, as an orange solid with purity greater than 99 A% and in greater than 80% yield.

NMR data (Coupling Constants (J) reported in hertz):

$^1$H NMR (400.13 MHz, DMSO-d$_6$)-data for the major rotamer δ 11.23 (s, 1H), 9.80 (s, 1H), 9.77 (s, 1H), 8.90 (d, J=8.4, 1H), 8.82 (d, J=8.4, 1H), 7.21 (br s, 1H), 7.01 (br s, 1H), 6.84 (overlapping m, 2H), 6.00 (d, J=8.0, 1H), 5.88 (t, J=3.6, 1H), 5.57 (d, J=2.4, 1H), 5.34 (d, J=4.4, 1H), 5.13 (d, J=4.4, 1H), 4.94 (d, J=4.4, 1H), 4.56 (t, J=5.6, 2H), 4.04 (dd, J=11.2, 3.2, 1H), 3.95 (overlapping m, 2H), 3.81 (dd, J=10.4,4.0, 1H), 3.53 (overlapping m, 6H);

$^{13}$C NMR (100.64 MHz, DMSO-d$_6$)-data for the major rotamer δ 169.03, 168.94, 157.79, 157.63, 144.38, 143.12, 129.46, 127.92, 125.19 (2C), 118.91, 117.57, 115.94, 114.32, 114.23, 113.92, 110.30, 110.24, 97.54, 97.49, 84.49, 78.39, 76.77, 72.88, 67.53, 62.59, 60.47 (2C), 58.33.21

| HPLC Analysis | | | |
|---|---|---|---|
| HPLC Parameters: | | | |
| Column: | YMC ODS-AQ (250 × 4.6 mm) | | |
| Flow rate: | 1.5 mL/min. | | |
| Detection: | 228 nm | | |
| Mobile Phase: | A = 0.1% H$_3$PO$_4$ aq | | |
| | B = acetonitrile | | |
| Gradient: | Min | A(%) | B(%) |
| | 0 | 85 | 15 |
| | 40 | 74 | 26 |
| | 60 | 30 | 70 |
| | 61 | 85 | 15 |
| | 65 | 85 | 15 |
| Injection Volume: | 10 μL | | |
| Temperature: | 25° C. | | |

What is claimed is:

1. A process for preparing crystals of compound I:

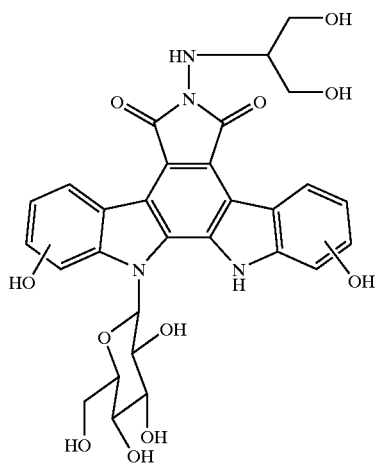

in high purity, which comprises the steps of:

(a) adjusting the pH of an acidic mixture consisting essentially of an acid, alcohol, water and compound I, by adding a base to produce a solution with a pH in the range of about 1.5 to about 6.5;

(b) keeping the temperature of the solution from step (a) in the range of about 50° C. to about 100° C. ; and (c) isolating the crystals of compound I.

2. The process according to claim 1, which comprises the steps of:

(a) adjusting the pH of an acidic mixture consisting essentially of an acid, alcohol, water and compound I, by adding a base to produce a solution with a pH in the range of about 1.5 to about 6.5;

(b) adjusting the solution from step (a) with an alcohol so that the solution is about 10% w/v to about 30% w/v water in an alcohol and the concentration of compound I is about 10 mL/g to 20 mL/g;

(c) adjusting the temperature of the solution from step (b) to a temperature in the range of about 50° C. to about 100° C. ;

(d) adding an alcohol to the solution from (c) such that the solution is diluted to about 3:2 (solution:alcohol);

(e) aging the solution from (d) at a temperature in the range of about 50° C. to about 100° C. until crystals of compound I are formed to produce a slurry; and (f) isolating the crystals of compound I.

3. The process according to claim 2, which further comprises deprotecting intermediate II:

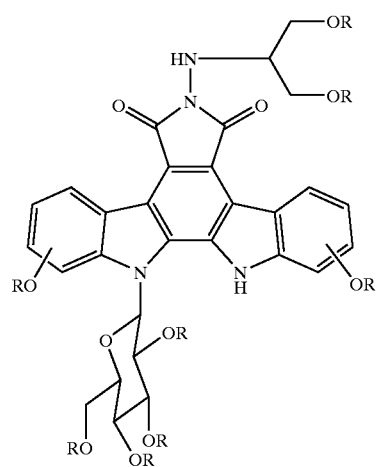

II (wherein R is independently a hydrogen or a substituted or unsubstituted benzyl protecting group, with the proviso that at least one R is a substituted or unsubstituted benzyl protecting group), via hydrogenation in the presence of a catalyst to produce a reaction mixture, followed by filtering the reaction mixture to afford the mixture of step (a).

4. The process according to claim 3, wherein R is benzyl.

5. A process for the preparation of compound III in high purity

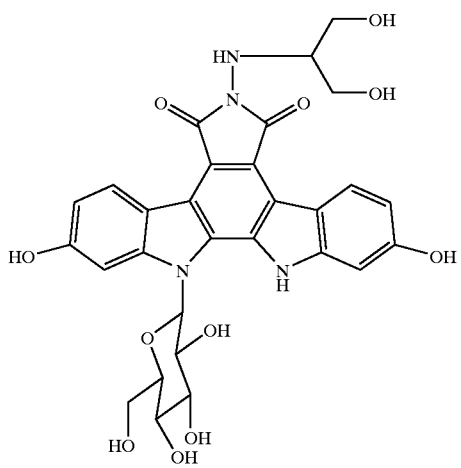

III which comprises the steps of:

(a) adjusting the pH of an acidic mixture consisting essentially of an acid, alcohol, water and compound III, by adding a base to produce a solution with a pH in the range of about 1.5 to about 6.5;

(b) adjusting the solution from step (a) with an alcohol so that the solution is about 10% w/v to about 30% w/v water in an alcohol and the concentration of compound III is about 10 mL/g to 20 mL/g;

(c) adjusting the temperature of the solution from step (b) to a temperature in the range of about 50° C. to about 100° C. ;

(d) seeding the solution;

(e) adding an alcohol to the solution such that the solution is diluted to about 3:2 (solution:alcohol);

(f) aging the solution from (e) at a temperature in the range of about 50° C. to about 100° C. until crystals of compound III are formed to produce a slurry; and (g) isolating the crystals of compound III.

6. The process according to claim 5, which further comprises deprotecting intermediate II:

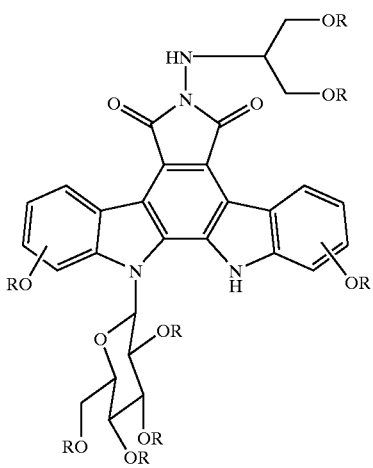

II (wherein R is independently a hydrogen or a substituted or unsubstituted benzyl protecting group, with the proviso that at least one R is a substituted or unsubstituted benzyl protecting group), via hydrogenation in the presence of a catalyst to produce a reaction mixture, followed by filtering the reaction mixture to afford the mixture of step (a).

7. The process according to claim 5 or 6, wherein the pH in step (a) is adjusted to a pH in the range of about 1.5 to about 3.5; the solution in (b) is adjusted so that the solution is about 15% w/v to about 25% w/v water in an alcohol and the concentration of compound III is about 12 mL/g to about 18 mL/g; and the temperature in step (c) is adjusted to about 70° C.

8. The process according to claim 7, wherein the pH in step (a) is adjusted to a pH of about 2.5; the solution in (b) is adjusted so that the solution is about 20% w/v water in an alcohol and the concentration of compound III is about 15 mL/g; and the temperature in step (c) is adjusted to about 70° C.

9. The process according to claim 8, further comprising the step of adjusting the slurry after step (f) such that the water content is lowered to a range of about 1% w/v to about 10% w/v before isolating the crystals of compound III in step (g).

10. The process according to claim 5, which comprises the steps of:

(a) adjusting the pH of an acidic mixture consisting essentially of an acid, alcohol, water and compound III, by adding a lower alkyl amine base to produce a solution with a pH of about 2.5;

(b) adjusting the solution from step (a) with isopropyl alcohol so that the solution is about 20% w/v water in isopropyl alcohol and the concentration of compound I is about 15 mL/g;

(c) adjusting the temperature of the solution from step (b) to a temperature of about 70° C.;

(d) seeding the solution;

(e) adding isopropyl alcohol to the solution such that the solution is diluted to about 3:2 (solution:isopropyl alcohol);

(f) aging the solution from (e) at a temperature of about 70° C. until the crystals of compound I are formed to produce a slurry;

(g) adjusting the slurry so that the water content is about 3% w/v;

(h) aging the slurry at about 70° C. before cooling down to about 22° C. ; and (i) isolating the crystals of compound III.

11. The process according to claim 10, which further comprises deprotecting intermediate II:

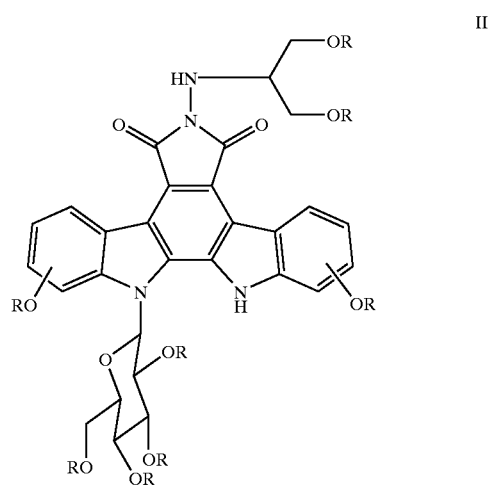

(wherein R is independently a hydrogen or a substituted or unsubstituted benzyl protecting group, with the proviso that at least one R is a substituted or unsubstituted benzyl protecting group), via hydrogenation in the presence of a catalyst to produce a reaction mixture, followed by filtering the reaction mixture to afford the mixture of step (a).

12. The process according to Claim II, wherein the lower alkyl amine in step (a) is triethylamine.

* * * * *